United States Patent [19]

Cepuritis

[11] 3,985,136

[45] Oct. 12, 1976

[54] TAB FASTENER HAVING FIXED END ANCHORED TO DIAPER FACING AND BACKING

[75] Inventor: Talivaldis Cepuritis, Kenilworth, Ill.

[73] Assignee: Johnson & Johnson, New Brunswick, N.J.

[22] Filed: Sept. 16, 1975

[21] Appl. No.: 613,782

[52] U.S. Cl. ............................... 128/287; 128/284
[51] Int. Cl.² .................... A61F 13/16; A41B 13/02
[58] Field of Search ................ 128/284, 287, 290 R, 128/290 H; 24/67, 73 VA, DIG. 11

[56] References Cited
UNITED STATES PATENTS

| | | | |
|---|---|---|---|
| 3,862,634 | 1/1975 | Small | 128/284 |
| 3,921,638 | 11/1975 | Schaar | 128/287 |
| 3,921,639 | 11/1975 | Cepuritis | 128/287 |
| 3,930,503 | 1/1976 | Tritsch | 128/287 |

Primary Examiner—Aldrich F. Medbery

[57] ABSTRACT

A disposable diaper having a facing sheet defining a diaper inside surface for direction toward an infant and a backing sheet defining a diaper outside surface is provided with adhesive tabs having a fixed end and free end. The fixed end of the tabs has an adhesive coating on both faces thereof, is interposed between the facing sheet and the backing sheet, and is permanently attached to opposing inner surfaces of the facing sheet and the backing sheet. The free end of the tab has an adhesive coating on one face thereof, is releasably attached to a release region provided on the diaper inside surface, and is movable from a folded-over storage position wherein the free end is releasably adhered to the release region to a working position wherein the adhesive coated free end is available for use in securing the diaper about an infant.

12 Claims, 5 Drawing Figures

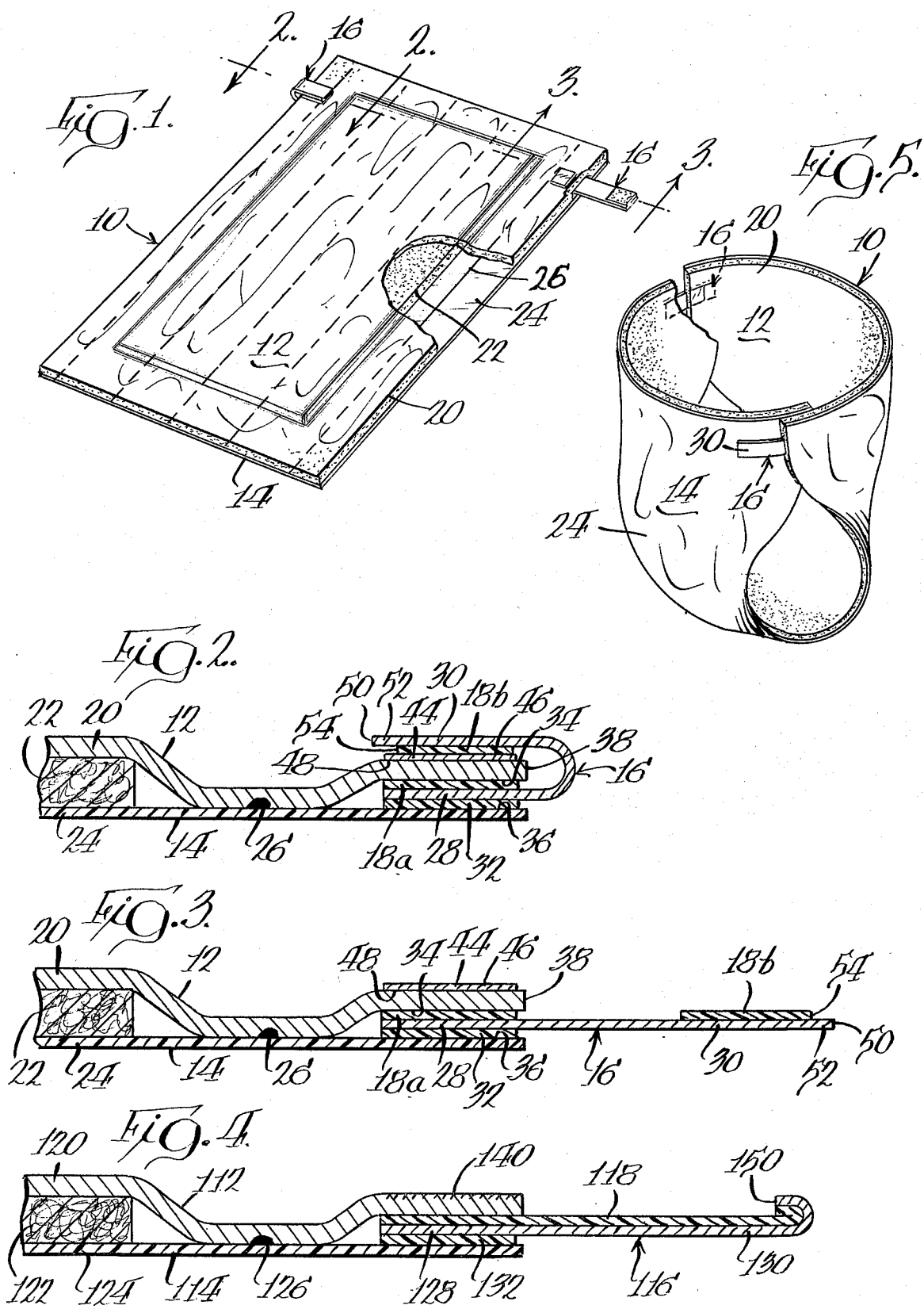

TAB FASTENER HAVING FIXED END ANCHORED TO DIAPER FACING AND BACKING

BACKGROUND OF THE INVENTION

This invention relates to disposable diapers. More particularly, this invention relates to disposable diapers adapted to be secured in place by adhesive tabs.

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a moisture-retaining layer of high liquid-holding capacity and a moisture-impervious backing sheet therefor, generally made of a plastic film such as polyethylene film or the like. Typical disposable diaper structures are shown in U.S. Pat. No. 3,612,055 to Mesek et al. and in U.S. Pat. No. Re. 26,151 to Duncan et al.

As may be seen from the above-cited patents, it is desirable to obviate the problems that are inherent in closure systems which utilize extraneous fasteners such as safety pins, snaps and zippers. To this end adhesive closure systems have presented acceptable solutions.

In order to protect the adhesive surfaces of the tape tabs, usually a cover strip having a release surface is applied over these adhesive surfaces for subsequent removal when the diaper is about to be used. However, such tabs usually project beyond the confines of the diaper to a considerable extent and interfere with the efficient manufacture and packaging of the diaper.

In an attempt to solve the foregoing problems, U.S. Pat. No. 3,646,937 to Gellert teaches a fastening tab which is provided with a release surface permanently bonded primarily to the inside surface of the diaper. One of the drawbacks of the Gellert arrangement is that in use the adhesive tape fasteners are permanently attached to only one surface of the diaper, generally the outside surface of the backing sheet, and thus the bond between one end of the tape fastener and the diaper backing sheet is subjected to all of the stresses exerted on the tape fastener during securement or as the infant moves about.

U.S. Pat. No. 3,750,669 to DeLuca shows a fastening tape provided with an adhesive end portion which extends beyond a cover strip for the tape and which is attached to a diaper inner covering or facing. However, such an adhesive end portion, when attached to a fibrous, non-woven facing fabric, may tear the facing fabric upon separation therefrom.

U.S. Pat. No. 3,776,234 to Hoey proposes to fold the tab over on itself at the diaper's edge and to adhesively attach a portion of the folded-over tab segment to an inwardly-folded margin of the diaper backing sheet in order to keep the tab flat against the diaper and thus from interfering with the manufacturing machinery and with the subsequent folding and packaging operations. This requires that the edge of the diaper backing sheet be folded over to present an attachment surface at the front or inside face of the diaper, and a relatively involved tab design is necessary for this purpose. Also, undesirable tearing of the diaper facing fabric may result if such a tab is inadvertently adhesively attached to the facing fabric of the diaper during manufacture.

U.S. Pat. No. 3,616,114 to Hamaguchi et al. discloses an adhesive sealing tape which can be used for releasably interconnecting parts of a diaper or other container. The fixed end of a main tape portion is attached to one side of a first container part. A reinforcing tape portion is provided with a turned up end which is attached to the undersurface of the midregion of the main tape portion, and a part of the reinforcing tape portion is attached to the opposite side of the first container part. The free end of the main tape portion is adapted for attachment to a second container part which is to be secured to the first container part. Thus, the Hamaguchi et al. patent requires two specially interconnected tape portions. Moreover, the turned up end of the reinforcing tape portion causes the folded configuration of the sealing tape to be somewhat bulky.

The adhesive fastener disclosed in U.S. Pat. No. 3,833,456 to Reed et al. can also be attached to both the front and back surfaces of a diaper to provide for force distribution over both surfaces. This particular fastener comprises two coextensive webs with each web having an adhesive coating extending along substantially all of one face. The lower or base web also has a release coating on one end portion of its opposite face so that a portion of the adhesive coating on the upper web is releasably secured thereto while the rest of the adhesive coating on the upper web bonds the two webs together. Since two substantially co-extensive webs are present, the fastener is bulky in the folded configuration, and is relatively expensive to manufacture.

A similar tape fastener is shown in U.S. Pat. No. 3,848,594 to Buell wherein the tape fastener is also attached to both the front and back surfaces of the diaper while having a securing portion attached to an adjacent section of the diaper, but has the disadvantage in that each tape fastener is comprised of two or more separate tape segments which are joined together so as to produce a common area of joinder for both fastener anchoring legs and the fastener securing portion and thereby adding complexities and expense to the manufacturing process, as well as requiring careful positioning during diaper manufacture.

SUMMARY OF THE INVENTION

According to the present invention, a single tape tab segment is used on each side of a diaper to secure the diaper about an infant. The tab has a fixed end and a free end. The fixed end is provided with adhesive coatings on both faces thereof, and is positioned between, and permanently attached to, opposing inner faces of the diaper facing sheet and backing sheet at substantially marginal locations thereof by means of the adhesive coatings. The opposite, outer face of the facing sheet defines the diaper inside surface. A release means which provides a release region is positioned at a marginal location on the inside surface. The free end of the tab is movable from a folded-over storage position, wherein an adhesive coating on one face of the free end is releasably adhered to the release region, to a working position wherein the adhesive-coated free end of the tab is available for use in securing the diaper about an infant.

The release means may comprise a release coating printed or otherwise deposited on a portion of the diaper inside surface, a release strip having a release coating on one face thereof and an adhesive coating on the opposite face by means of which the release strip is adhered to the diaper, or other suitable means for releasably adhering the free end of the tab to the diaper.

Gripping means may also be provided on the tab to facilitate separation of the free end of the tab from the release means preparatory to fastening the diaper about an infant.

The tape tab fasteners of the present invention remain flat against the diaper when in the folded configuration and will not interfere with the diaper manufacturing machinery and the subsequent folding and packaging operations. It is another advantage of the present invention that the tape tab is relatively compact in the folded configuration. Additional features of this invention include the utilization of an integral tape tab which is relatively inexpensive and simple to manufacture, and permanent attachment of the tab to both the diaper facing sheet and backing sheet so that when stress is imposed on the free end which fastens the diaper, the stress is distributed between the facing sheet and the backing sheet, thereby reducing the possibility of undesirable rupture of the backing sheet.

BRIEF DESCRIPTION OF THE DRAWINGS

FIG. 1 is a perspective view, partially broken away to show interior detail, of an open unfolded diaper in accordance with one of the embodiments of the invention;

FIG. 2 is an enlarged fragmentary cross-sectional view of the diaper of FIG. 1 taken along plane 2—2;

FIG. 3 is an enlarged fragmentary cross-sectional view of the diaper of FIG. 1 taken along plane 3—3;

FIG. 4 is a fragmentary cross-sectional view, similar to FIG. 3, and illustrating an alternate embodiment of the invention; and FIG. 5 is a perspective view of the diaper of FIG. 1 in a configuration assumed by the diaper when placed about an infant.

DESCRIPTION OF THE PREFERRED EMBODIMENTS

In the following description, two digit numerals are used to refer to the embodiment illustrated in FIGS. 1–3 and 5, and three digit numerals in the one hundred series are used to refer to the embodiment illustrated in FIG. 4, the same last two digits in each numeral designating similar elements in the various embodiments.

Disposable diaper 10, illustrated in FIGS. 1 and 5, is of substantially quadrilateral configuration and presents inside surface 12 for direction toward an infant and outside surface 14 for direction away from the infant. Adhesive tab fastener means such as tab 16 are attached to diaper 10 for securing diaper 10 about an infant. As described in greater detail below, tab 16 is movable from a folded-over storage position illustrated in FIG. 2 to a working position which is illustrated in FIG. 3. Portions of the face of tab 16 which faces in the same direction as the diaper inside surface 12 are provided with a pressure-sensitive adhesive coating 18.

Referring to FIGS. 1–3, diaper 10 comprises moisture-previous facing sheet 20 which defines diaper inside surface 12, overlying a moisture-retaining absorbent pad 22, and backing sheet 24 which is made of a moisture-impervious material and defines diaper outside surface 14. Absorbent pad 22 is somewhat smaller than the backing sheet 24 and is centrally disposed thereon; however, absorbent pad 22 can be made co-extensive with backing sheet 24, if desired. Facing sheet 20 is substantially co-extensive with backing sheet 24. Both the facing sheet 20 and pad 22 can be anchored to the backing sheet 24 by means of adhesive beads 26, glue spots or in any other convenient manner. For example, if backing sheet 24 is made of a thermoplastic material, facing sheet 20 and pad 22 can be attached thereto by heat bonding.

As illustrated in FIGS. 2 and 3, adhesive tab 16 has fixed end portion 28 and free working end portion 30. Fixed end 28 bears adhesive coating 18a on one face thereof, and adhesive coating 32 on the opposite face thereof. The fixed end 28 of tape tab 16 is positioned between facing sheet 20 and backing sheet 24, and is permanently attached by means of adhesive coatings 18a and 32 to facing sheet 20 and backing sheet 24 at substantially juxtaposed marginal locations thereon. Adhesive coating 18a is attached to surface 34 of the facing sheet 20 opposite diaper inside surface 12, and the adhesive coating 32 is attached to surface 36 of backing sheet 24 opposite diaper outside surface 14, so that stresses exerted on tab 16 are distributed to both facing sheet 10 and backing sheet 24. Adhesive coatings 18a and 32 can be made of a pressure-sensitive adhesive composition, a heat-activated or solvent-activated adhesive composition or the like.

Referring to FIGS. 2 and 3, tab 16 is folded about longitudinal edge 38 of diaper 10, and end portions 28 and 30 of tab 16 preferably are about equal in length. Free end 30 provides a securement means for fastening the diaper about an infant and can be moved from the closed storage position of FIG. 2 to the open working position of FIG. 3. Free end 30 is provided with an adhesive coating 18b which faces in the same direction as the diaper inside surface 12 when the tab 16 is in the working position. Adhesive coating 18b preferably is made of a pressure-sensitive adhesive composition.

A release means is provided and is adapted to be releasably attached to adhesive coating 18b. The release means may be carried by diaper 10 at a marginal location thereon to provide a release region on diaper inside surface 12. Various embodiments are contemplated in which a release region, which may comprise a release surface or layer, is provided between adhesive coating 18b on free end 30 and diaper inside surface 12 which is juxtaposed to free end 30 when tab 16 is in the folded-over, closed position. In the embodiment illustrated in FIGS. 2 and 3, the release surface comprises a ribbon segment or release strip 44 having a release coated surface on face 46 which provides a release region, and an adhesive coating on opposite face 48 by means of which release strip 44 is anchored to diaper inside surface 12. Release strip 44 preferably provides a release region of about the same width as tab 16, but may have a width greater than the width of the tab 16.

In the embodiment illustrated in FIG. 4, tab fastener means 116 includes a release layer 140 which comprises a surface coating on a marginal portion of the diaper inside surface 112. The release coating is at least as wide as the tab 116 and preferably comprises a silicone release compound, or the like.

Adhesive coating 18 on fixed end 28 and free end 30 of tab 16 may be spaced from one another as shown in FIGS. 2 and 3 wherein adhesive coatings 18a and 18b are provided, or may comprise continuous layer 118 of a pressure-sensitive adhesive as illustrated in FIG. 4. The continuous layer of adhesive is easier to manufacture; however, less adhesive is required where the adhesive coatings are spaced from one another.

It is desirable to provide a gripping means to facilitate separation of free end 30 of tab 16 from the release means preparatory to fastening the diaper about an infant. As is shown in FIGS. 2 and 3, free end 30 of tab 16 can be provided with a projecting portion 52 which extends beyond outermost margin or edge 54 of adhesive coating 18b, whereby outwardly extending portion 52 provides a gripping means for removing free end 30 from the release means when fastening diaper 10 about an infant. Alternatively, the release means which comprises the release strip 44 can be provided with a longitudinal dimension which is greater than the longitudinal dimension of the free end 30 to enable a user to more easily grasp free working end 30. In FIG. 4, a terminal segment of free end 130 adjacent the distal end 150 thereof is folded over upon itself so that adhesive coating 118 is juxtaposed to itself, thereby providing a gripping tab means. Two or more of the above modifications may be simultaneously used to facilitate gripping the distal end 50 of free end 30.

Adhesive tabs suitable for the purposes of the present invention can be made from a wide variety of materials, provided that such materials are sufficiently flexible. Preferred materials for this purpose are polyalkylene webs such as polyethylene sheet, polypropylene sheet, and the like. Particularly preferred are webs which are oriented along the narrow dimension of the tab or webs which have filament reinforcements therein.

The pressure-sensitive adhesive layers such as adhesive coating 18b are provided by applying a coating of a pressure-sensitive adhesive composition known in the art to the appropriate surface of tab 16. The applied adhesive shall have good tack, good cohesive strength, good resistance to moisture and good resistance to aging. Illustrative of such adhesive compositions are mixtures of natural or synthetic rubber, zinc oxide, and various resins, also latices of natural or synthetic rubber, or water dispersions of acrylic tacky polymers or copolymers, and the like.

Anchored release strips 44 can be made from smooth plastic film having a relatively non-adhering surface, from paper coated with a silicone release compound, or from similar release materials. A number of appropriate release coatings may be used with the present invention. Examples of such coatings are disclosed in U.S. Pat. No. 2,822,290 to Webber; U.S. Pat. No. 2,880,862 to Sermattei; and U.S. Pat. No. 2,985,554 to Dickard.

Several different types of facing materials may be used for diaper facing sheet 20. For example, facing sheet 20 may be made up of a mixture of fibers consisting predominantly of inexpensive short cellulosic fibers such as wood pulp fibers or cotton linters, in amounts of about 75% to about 98%, the balance being textile length fibers such as rayon as described in U.S. Pat. No. 3,663,348 to Liloia et al.

Facing sheet materials suitable for use in this invention can have fabric weights in the range of about 1 to 5 oz./yd.$^2$ and densities of less than 0.15 g./cc., generally in the range between 0.05 and 0.1 g./cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 20 may also be made of an apertured, nonwoven fabric which is formed, for example, in accordance with the teachings of commonly assigned U.S. Pat. Nos. 2,862,251; 3,081,514 and 3,081,515.

Briefly, such fabrics are foraminous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd$^2$.

In addition, facing sheet 20 can be formed of a non-apertured material, such as a nonwoven isotropic web, or the like. In all of the aforementioned facing materials, the material should be relatively hydrophobic so as to retard wicking within the facing layer. Also suitable are porous polymeric sheet materials such as polyalkylene webs having a fibrous surface, and the like.

Highly moisture-absorbent fibrous pad or batt 22, which usually is substantially rectangular in shape but smaller than the facing sheet and the backing sheet, can be formed in accordance with the teachings of U.S. Pat. No. 3,612,055 to Mesek et al. If desired, a highly moisture-absorbent layer can be provided substantially coextensive with backing sheet 24 and facing sheet 20.

A suitable backing sheet material for the diapers embodying the present invention can be an opaque polyethylene web about 0.001'' thick. Another suitable material for this purpose is a polyethylene terephthalate web having a thickness of about 0.0005''. Typical disposable diapers which can be fitted with tab-type adhesive fasteners described hereinabove are shown in U.S. Pat. No. 3,612,055 to Mesek et al. and in U.S. Pat. No. 3,683,916 to Mesek et al. Other suitable disposable diaper structures which can be improved by the present tab-type fasteners are shown in U.S. Pat. No. Re. 26,151 to Duncan et al.

In use, a diaper equipped with the adhesive fasteners of the present invention is applied to the infant by laying out the diaper on a suitable flat surface and placing the infant thereon so that the waist-underlying end of the diaper is that having the tab fastener means. The other end of the diaper then extends downwardly between the infant's legs. Next, the downwardly extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive fasteners are than prepared for use by pulling free end portions 30 away from their temporary engagement with the release means such as release regions 44 on facing sheet 20, grasping the exposed free end portions and pulling the free end portions away from the release region 44 which is releasably adhered to adhesive coating 18b on free end portion 30 and separable therefrom. The tabs are then used to secure the diaper in the desired position by simply urging the pressure-sensitive adhesive surfaces in contact with the adjacent outer surface of the diaper.

The applied diaper assumes the configuration illustrated in FIG. 5.

The foregoing description and the drawing are illustrative but are not to be taken as limiting. Still other variations and modifications are possible without departing from the spirit and scope of the present invention.

I claim:

1. A disposable diaper having a facing sheet defining a diaper inside surface for direction toward an infant, a moisture-impervious backing sheet substantially coextensive with said facing sheet and defining a diaper outside surface, an absorbent panel positioned between said facing sheet and said backing sheet, and an adhesive tab fastener means which comprises:

an elongated tape segment attached to said diaper at a marginal location thereof, having a fixed end provided with an adhesive coating on both faces thereof and a free end;

a pressure-sensitive adhesive coating on one face of said free end; and release means releasably attached to said adhesive coating on said free end;

said fixed end of said tape segment being positioned between said facing sheet and said backing sheet and being permanently attached by means of said adhesive coatings to said facing sheet and to said backing sheet at substantially juxtaposed marginal locations thereof; and said free end being separable from said release means to make said adhesive-coated free end of said tape segment available for use in securing said diaper about an infant.

2. The disposable diaper as defined in claim 1 wherein said adhesive coating on the fixed end of said tape segment and said adhesive coating on the free end of said tape segment are provided by a continuous layer of a pressure-sensitive adhesive on said tape segment.

3. The disposable diaper as defined in claim 1 wherein said adhesive coating on the free end of said tape segment and said adhesive coating on the face of the fixed end of said tape segment which is attached to said facing sheet are spaced from one another.

4. The disposable diaper as defined in claim 1 wherein said release means is carried by said diaper at a marginal location thereon and provides a release region facing in the same direction as said diaper inside surface, said free end being movable from a folded-over storage position wherein said free end is releasably adhered to said release region to a working position wherein said adhesive-coated free end of said tape segment is available for use in securing said diaper about an infant.

5. The disposable diaper as defined in claim 4 wherein said adhesive coating on said free end faces in the same direction as said diaper inside surface when said tab fastener is in said working position.

6. The disposable diaper as defined in claim 4 wherein said release means is a release coating on a portion of said diaper inside surface.

7. The disposable diaper as defined in claim 6 wherein said release coating comprises a silicone release compound.

8. The disposable diaper as defined in claim 4 wherein said release means comprises a ribbon segment which has one face adhesively affixed to the inside surface of said diaper and an opposite face having a release coating.

9. The disposable diaper as defined in claim 4 wherein said release means has a width greater than the width of said tape segment.

10. The disposable diaper as defined in claim 4 wherein a portion of said tape segment adjacent the distal end of said free end is folded over to provide a gripping means for separating said tape segment from said release means when fastening said diaper about said infant.

11. The disposable diaper as defined in claim 4 wherein said release means has a longitudinal dimension greater than said free end to facilitate gripping said free end for separating said tape segment from said release means when fastening said diaper about said infant.

12. The disposable diaper as defined in claim 4 wherein a portion of said free end of said tape segment projects beyond the outermost edge of said adhesive coating on said free end of said tape segment, whereby said projecting portion of said tape segment provides a gripping means for separating said tape segment from said release means when fastening said diaper about said infant.

* * * * *